United States Patent [19]

Margolis et al.

[11] 4,234,258
[45] Nov. 18, 1980

[54] STARK CELL OPTOACOUSTIC DETECTION OF CONSTITUENT GASES IN SAMPLE

[76] Inventors: Robert A. Frosch, Administrator of the National Aeronautics and Space Administration, with respect to an invention of Jack S. Margolis, Pasadena, Calif.; Michael S. Shumate, Pasadena, Calif.

[21] Appl. No.: 938,297

[22] Filed: Aug. 31, 1978

[51] Int. Cl.³ .......................................... G01N 21/39
[52] U.S. Cl. ..................................... 356/437; 250/343
[58] Field of Search ............... 356/319, 323, 326, 432, 356/437; 250/343, 344

[56] References Cited

U.S. PATENT DOCUMENTS 4,105,919   8/1978   Bridges et al. ................. 250/343 X

*Primary Examiner*—F. L. Evans
*Attorney, Agent, or Firm*—Monte F. Mott; John R. Manning; Paul F. McCaul

[57] ABSTRACT

An optoacoustic detector for gas analysis is implemented with Stark-effect cell modulation for switching a beam in and out of coincidence with a spectral line of a constituent gas in order to eliminate the heating effect of laser energy in the cell as a source of background noise. By using a multiline laser, and linearly sweeping the DC bias voltage while exciting the cell with a multiline laser, it is possible to obtain a spectrum from which to determine the combination of excited constituents and determine their concentrations in parts per million.

10 Claims, 5 Drawing Figures

STARK CELL OPTOACOUSTIC DETECTION OF CONSTITUENT GASES IN SAMPLE

ORIGIN OF INVENTION

The invention described herein was made in the performance of work under a NASA contract and is subject to the provisions of Section 305 of the National Aeronautics and Space Act of 1958, Public Law 85-568 (72 Stat. 435; U.S.C. 2457).

BACKGROUND OF THE INVENTION

This invention relates to a method and apparatus for a multiline laser optoacoustic detection, and more particularly to an improved optoacoustic detector, and a method of using such an improved optoacoustic detector, for determining the combination of constituent gases in a sample, and determining the concentration in parts per million of each constituent.

Optoacoustic detectors have become very promising for gas analysis in recent years. See "Laser Optoacoustic Spectroscopy-A New Technique of Gas Analysis by L. B. Kreuzer," Analytical Chemistry, Vol. 46, No. 2., February 1974 pp 2394A–244A, and "Excited-State Spectroscopy of Molecules Using Opto-acoustic Detection" by C.K.N. Patel, et al., Physical Review Letters, Vol. 38, No. 21, May 1977, pp 1204–1207. The effort is now being made to improve the sensitivity of optoacoustic detectors.

Briefly, an optoacoustic detector operates by sensing pressure pulses induced in a gas sample by absorption of chopped laser radiation passing through it. The laser is tuned to different wavelengths to detect the presence of different constituent gases in the sample. Assuming that no energy is absorbed by the sample cell, the energy absorbed by the sample during each light pulse will increase the pressure of the gas in the sample cell in proportion to the amount of the absorbing gas present. This pressure pulse may be detected by a microphone, hence the term optoacoustic detector for the sample cell and microphone. The problem is that in practice the windows through which the laser beam passes through the cell will absorb some energy and introduce acoustical noise in the system. Efforts made in the past to cope with this acoustical noise have not been totally satisfactory. It would be preferable to devise an optoacoustic detector which eliminates the acoustical noise generated by heating of the windows.

SUMMARY OF THE INVENTION

In accordance with the present invention, a CW laser beam having a spectral line coincident with an absorption line of a constituent of a gas sample in a closed cell is directed through windows in the cell to interact with the absorbing constituents. The interaction between the laser and an absorbing constituent causes a pressure proportional to the absorption coefficient of a constituent. Many gases possess a dipole moment, and will consequently have absorption frequencies that will exhibit the Stark effect, in which selected absorption features can be modified in the presence of a static electric field. The pressure is detected by a microphone while an electric field between two parallel plates is modulated to move the spectral absorption line in and out of coincidence with the laser line. This is accomplished by a DC power source biasing the plates while a squarewave generator modulates the bias. This Stark Cell modulation technique moves the absorption line of the absorbing constituent inside the cell to exactly coincide with the laser spectral line (a beam ON condition) producing a pressure increase due to heating, and alternately to a position away from the laser line (a beam OFF condition). The difference in pressure between the ON and OFF condition indicates the presence of the constituent, and the amplitude of the peak indicates the quantity (parts per million) of the constituent. The presence of all constituents of interest may thus be detected and measured by varying the laser frequency because the electric field dependence of the spectrophone will be due to absorption of any of the resonating laser line and will be unique to the constituent in the spectrophone cell. A multiline laser may be used to excite the spectrophone cell, in which case the electric field dependence of the composite response produces a composite absorption which is unique and therefore determines the combination of excited constituents in the spectrophone cell, i.e., produces a signature of the particular gas in the spectrophone cell.

The novel features that are considered characteristic of this invention are set forth with particularity in the appended claims. The invention will best be understood from the following description when read in connection with the accompanying drawings.

DESCRIPTION OF THE DRAWINGS

Figure 1:
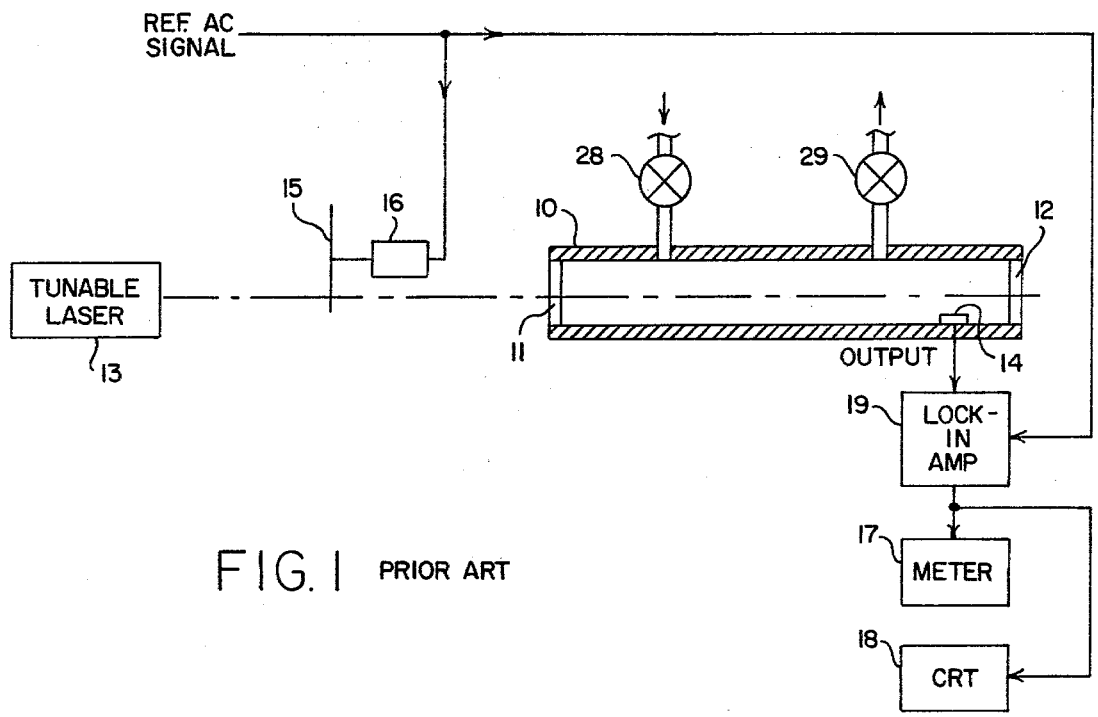
FIG. 1 is a schematic diagram of a prior art spectrophone.

Referring first to the prior art shown in FIG. 1, a spectrophone cell 10 is provided with ZnSe windows 11 and 12 in the opposite ends so that a beam from a tunable laser 13 can be directed through the cell. A pressure transducer (microphone) 14 is in communication with the gas in the cell 10.

The gas within the cell can be excited by the laser beam if its absorption frequency (spectral line) is the same as the laser frequency (line). This excitation manifests itself as heat causing the pressure in the cell to increase. If the laser beam is modulated at an audio frequency, as by interrupting the beam with a chopper wheel 15 driven by an AC synchronous motor 16, a pressure change at the audio frequency is detected by the microphone and amplified for display on a meter 17 or cathode ray tube 18 using a lock-in amplifier 19. The magnitude of this change is proportional to the absorption of the sample at the laser frequency, and is a function of its absorption coefficient and quantity (parts per million). The presence of a constituent may thus be detected by a peak signal at the spectral line of the constituent if the laser is tuned across the spectral line, and the parts per million of the constituent may be determined from the amplitude of the peak. However, the true amplitude of the peak is obscured in that the baseline may shift due to increase pressure in the cell caused not by absorption of laser energy by the gas but by the windows at each end. U.S. Pat. Nos. 3,995,960 and 4,067,653 disclose spectrophone cell designs which reduce this background pressure significantly, but the object of this invention is to eliminate the effect of window heating on the absorption pressure measurement.

Figure 2:
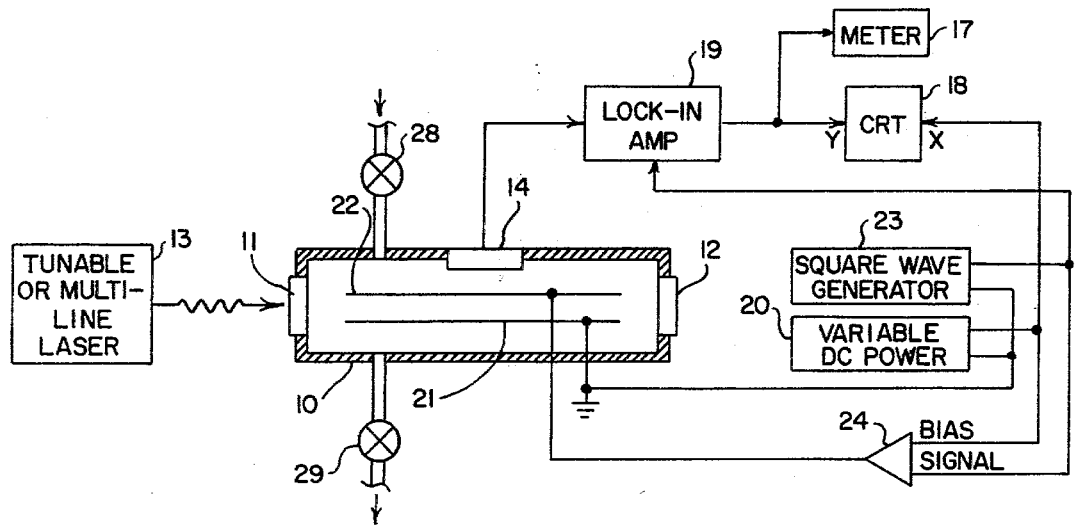
FIG. 2 is a schematic diagram of the present invention.

Referring now to FIG. 2, wherein components common to the prior art system are referred to by the same reference numerals as in FIG. 1, and other figures, the laser is not modulated externally by a chopper. Instead, a DC voltage from a source 20 is applied to parallel plates 21 and 22 in the cell 10 to produce an electric field at a voltage level adjusted to bias the spectral line of the gas constituent of interest onto the laser spectral line, i.e., to bias the center frequency of the absorption resonance of the constituent gas at the laser frequency, thus transforming the cell 10 into a Stark effect cell. A square-wave generator 23 applies an AC reference signal to the plates via a differential amplifier 24 to vary the spectral line (absorption resonance of the constituent gas) about the laser frequency. That effectively modulates the laser beam passing through the cell ON and OFF with respect to the spectral line. The presence of the constituent may thus be detected by a peak signal at the spectral line for the constituent, and the parts per million of the constituent determined from the amplitude of the pressure modulation peaks. In that manner, the laser beam can be operated continuously as a CW laser without external ON and OFF states. Pressure differential due to heating of the windows is thus eliminated from the measurement of the spectral line pressure output. This is because the pressure due to heating of the windows affects the pressure level during both the internal ON and OFF states.

The effect of the bias switching is to cause a modulated electric field to be created between the plates 21 and 22, the magnitude of which causes a reaction with polar molecular gases, such as water vapor, atmospheric fluorocarbons, and some nitrous and nitric compounds of interest for detecting explosives, and many others having a dipole moment. It is thus possible to tune the spectral lines of gas constituents of interest across the laser spectral line and detect the constituents gases of the sample in the Stark-effect spectrophone cell.

Figure 3:
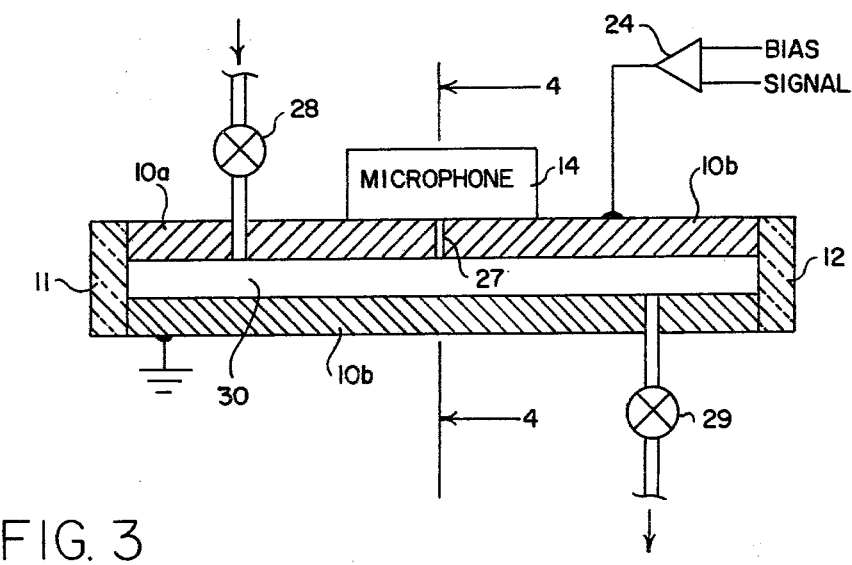
FIG. 3 illustrates a preferred arrangement for electric field plates in the spectrophone cell of FIG. 2.
Figure 4:
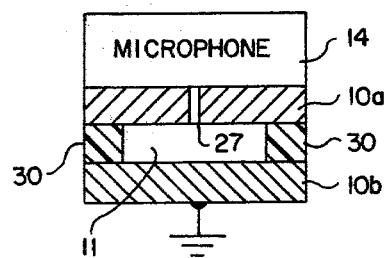
FIG. 4 is a cross section of FIG. 3 taken along a line 4—4.

FIGS. 3 and 4 illustrates schematically a preferred structure for the Stark-effect spectrophone cell, with the plates being incorporated into the cell walls, and spaced apart a minimum distance necessary to allow the laser beam to pass. The microphone is mounted outside the cell, but placed in direct pressure communication with the cell by a port 27. Gas to be analyzed is introduced through a valve 28 after all gas in the cell has been previously pumped out through a valve 29. The high voltage plate is electrically insulated from the ground plate by a dielectric material 30 such as glass.

Figure 5:
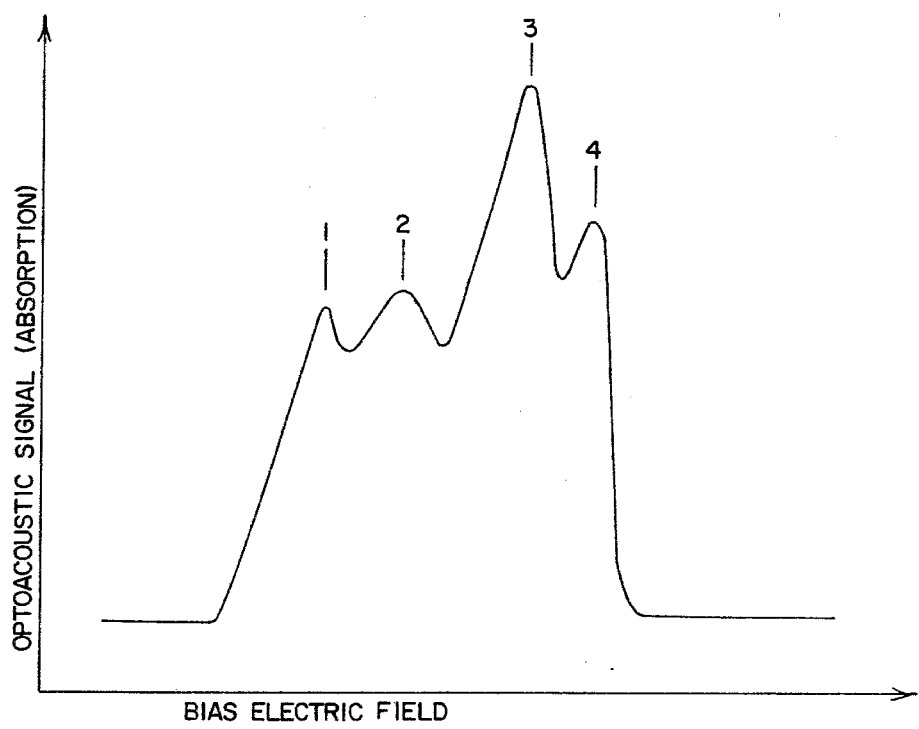
FIG. 5 is a typical "signature" of a particular gas in the spectrophone cell of FIG. 2.

The principal advantage of the Stark-effect spectrophone cell is elimination of window heating as a source of noise in the measurement of the parts per million of constituent gases, but another important advantage is that it makes it possible to distinguish the absorption from different molecules because the electric field in the Stark cell will modulate the absorption of different molecules in different ways, i.e., because application of an electric field to the gas molecules inside the optoacoustic detector perturbs the absorption frequencies of those molecules. This makes the spectrophone a more selective instrument, and if a laser emitting more than one frequency is used to excite the spectrophone, the electric field dependence of the spectrophone signal output will be due to absorption of any of the resonating laser lines and will be unique to the gas in the spectrophone. The signal output plotted as a function of electric field applied will thus be a "signature" of the combination of excited constituents in the sample. FIG. 5 illustrates a typical plot made as the bias voltage is swept linearly from a low level to a high level while the output of the squarewave generator is superimposed on the bias to switch the bias ON and OFF at the desired frequency to be modulated on the absorbing constituents of the gas within the cell.

In interpreting the data plotted, the specific level of the electric field is one parameter used to distinguish each specific gas constituent creating the various peaks 1, 2, 3 and 4. The other parameter is the input laser lines since coincidence of the laser lines and the Stark-effect modulated absorption lines are necessary for spectrophone output. By experimenting with known combinations of gases, using the appropriate laser lines, a "signature" like the plot shown in FIG. 5 may be obtained for each combination of interest, such as in monitoring the atmosphere for known pollutants. In addition, for each combination producing a unique pattern of peaks, it is possible to produce a library of plots for different quantities of the constituents. In that manner, the parts per million of a particular constituent in a combination may be determined as a function of the peak amplitude in that combination. This multiline laser application of the Stark-effect optoacoustic detector will facilitate gas analysis where the combination of gases expected is known, and the purpose of the analysis is to monitor the parts per million of the constituents.

Although particular embodiments of the invention have been described and illustrated herein, it is recognized that modifications and variations may readily occur to those skilled in the art. It is therefore intended that the claims be interpreted to cover such modifications and variations.

What is claimed is:

1. A method for gas analysis using the Stark effect comprising the steps of generating a laser beam having at least one predetermined spectral line frequency, placing a gas sample in a cell in the path of said laser beam, said cell having windows for said beam to pass, and plates parallel to said beam and parallel to each other, one plate on each side of said beam, applying a bias voltage to said plates to adjust the absorption line of a predetermined constituent suspected to be present in said gas sample into coincidence with said laser spectral line, modulating said bias voltage applied to said plates to move the absorption line of said constituent alternately in and out of coincidence with said laser spectral line, and sensing pressure variations of said gas in said cell during modulation of said bias voltage to determine the presence of said constituent from a peak absorption at the absorption line of said constituent, and to determine the parts per million of said constituent from the amplitude of said peak.

2. The method of claim 1 wherein said gas sample contains a plurality of suspected constituents, each having a predetermined distinct absorption line, including the step of tuning the spectral line frequencies of said laser onto said absorption lines of said constituents while continuing to modulate said bias voltage as for one constituent, and detecting the presence of said constituents from the predetermined absorption lines, and the parts per million of said constituents from the amplitudes of said peaks.

3. The method of claim 1 wherein said gas sample contains a plurality of suspected constituents, each having a distinct predetermined absorption line, including the step of producing multiple spectral line frequencies of said laser to include said absorption lines of said constituents and sweeping said bias voltage while continuing to modulate said bias voltage as for one constituent, thereby to obtain a composite response, plotting said pressure variations as a function of said bias, and determining whether said gas sample contains specific combinations of constituents, and the parts per million of said constituents from peaks of said composite response plotted as a function of said bias.

4. Apparatus for gas analysis using the Stark effect comprising
   means for generating a laser beam having at least one predetermined spectral line frequency,
   a gas sample cell in the path of said laser beam, said cell having windows for said beam to pass, and electrically isolated plates parallel to said beam and parallel to each other, one plate on each side of said beam,
   means for applying a bias voltage to said plates to create an electric field between said plates which will adjust the absorption line of a predetermined constituent suspected to be present in said gas sample into coincidence with said laser spectral line,
   means for modulating said bias voltage applied to said plates to move the absorption line of said constituent alternately in and out of coincidence with said laser spectral line,
   means for sensing pressure variations of said gas in said cell during modulation of said bias voltage, and
   means for displaying said pressure variations as a function of said bias voltage to determine the presence of said constituent from a peak absorption at the absorption line of said constituent, and to determine the parts per million of said constituent from the amplitude of said peak.

5. Apparatus as defined in claim 4, wherein said gas sample contains a plurality of suspected constituents, each having a predetermined distinct absorption line, and means for tuning spectral lines of said laser onto said absorption lines of said constituents while continuing to modulate said bias voltage as for one constituent, and detecting the presence of said constituents from the predetermined absorption lines, and the parts per million of said constituents from the amplitudes of said peaks.

6. Apparatus as defined in claim 4, wherein said gas sample contains a plurality of suspected constituents, each having a distinct predetermined absorption line, and said laser produces multiple spectral lines which include said absorption lines of said constituents, and means for sweeping said bias voltage while continuing to modulate said bias voltage as for one constituent, thereby to obtain a composite response for plotting as a function of said bias, thereby to determine whether said gas sample contains specific combinations of constituents and the parts per million of said constituents from peaks of said composite response plotted as a function of said bias.

7. Apparatus as defined in claim 4 wherein said electrically isolated plates are opposing walls of said cell isolated from each other by side walls of dielectric material.

8. Apparatus as defined in claim 7 wherein said plates are spaced apart a minimum distance necessary to pass said laser beam.

9. In an optoacoustic detector for analysis of a gas in a cell using a laser beam having a known spectral line directed to pass through the cell, where said cell has a transparent window at each end, a method of eliminating the heating effect of laser energy in said cell due to energy absorbed from said laser beam by said windows comprised of the steps of providing an electric field perpendicular to the path of said laser beam through said cell and adjusting said field to bias the absorption line of a gas constituent into coincidence with said laser spectral line, and modulating said field into and out of coincidence with said laser spectral line.

10. In an optoacoustic detector, a method as defined in claim 9 wherein said laser beam has a plurality of known laser spectral lines, whereby the electric field dependence of the absorption is the sum of the absorption due to the individual laser beam spectral lines and the composite absorption is unique to the particular gas having a plurality of constituents, and including the step of sweeping the electric field from a low level to a high level sufficient to span absorption peaks of the sample gas constituents.

* * * * *